United States Patent [19]

Ishibashi et al.

[11] Patent Number: 4,822,785
[45] Date of Patent: Apr. 18, 1989

[54] CEPHALOSPORIN INJECTION

[75] Inventors: Yasuo Ishibashi, Gifu; Muneaki Matsuda, Ichinomiya; Kazuhide Ashizawa, Ibaraki, all of Japan

[73] Assignee: Eisai Co., Ltd., Tokyo, Japan

[21] Appl. No.: 67,507

[22] Filed: Jun. 26, 1987

[30] Foreign Application Priority Data

Jul. 10, 1986 [JP] Japan ................ 61-160746

[51] Int. Cl.$^4$ ............................ A61K 31/545
[52] U.S. Cl. ................................... 514/202
[58] Field of Search ........................ 514/202

[56] References Cited

U.S. PATENT DOCUMENTS 4,278,671  7/1981  Ochiai et al. ............. 514/203
4,525,473  6/1985  Aburaki et al. ............ 544/22
4,748,171  5/1988  Yamauchi et al. .......... 514/202

FOREIGN PATENT DOCUMENTS 0188255A  7/1986  European Pat. Off. ........ 514/202

OTHER PUBLICATIONS

Chemical Abstracts 91:27333u (1979).
Chemical Abstracts 92:153141w (1980).

Primary Examiner—Jerome D. Goldberg
Attorney, Agent, or Firm—Flynn, Thiel, Boutell & Tanis

[57] ABSTRACT

A cephalosporin having the formula

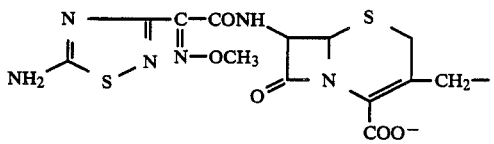
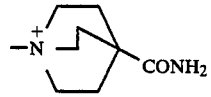

is stabilized in an injection solution with lactose and/or sodium chloride.

10 Claims, No Drawings

CEPHALOSPORIN INJECTION

The present invention relates to a cephalosporin injection. Thus the present invention is employed in the field of medicines.

A cephalosporin of the following general formula:

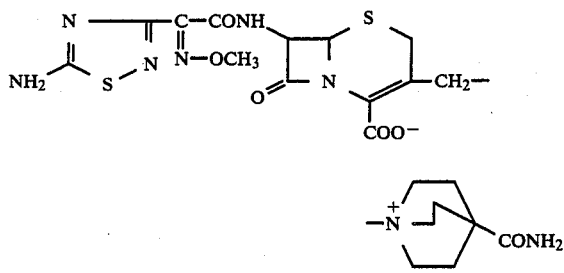

i.e. 7β-[(Z)-2-(5-amino-1,2,4-thiadiazol-3-yl)-2-methoxyiminoacetamido]-3-(4-carbamoyl-1-quinuclidinio)-methyl-3-cephem-4-carboxylate and nontoxic salts thereof are denoted here as cephalosporin and have a strong antibacterial activity against Gram-negative bacilli of glucose non-fermentation type, such as Pseudomonas aeruginosa and Acinetobacter. Therefore, it would be expected to use them in injections against these bacilli. Since, however, these compounds are chemically unstable, coloration and reduction in the titer of them are observed in not only aqueous solutions but also dry powders. These phenomena are observed to proceed, for example, even in a powdery cephalosporin, which is to be dissolved in situ to form an injection, as time elapses. No satisfactory means of solving this problem has been developed yet.

Under these circumstances, the inventors have sought a composition of an injection of the cephalosporin of the present invention in powdery form which is to be dissolved in situ and which can be protected from the coloration or reduction in the titer during storage. As a result, the inventors have found that the problem can be solved by incorporating one or both of lactose and sodium chloride in the above injection. The present invention has been completed on the basis of this finding.

Now, the detailed description will be made on the present invention.

The cephalosporin according to the present invention is 7β-[(Z)-2-(5-amino-1,2,4-thiadiazol-3-yl)-2-methoxyiminoacetamido]-3-(4-carbamoyl-1-quinuclidinio)-methyl-3-cephem-4-carboxylate or its nontoxic salt and is used as an injection. For example, 500 to 1,000 mg of the cephalosporin is administered by instillation. The cephalosporins have a wide anti-microbial spectrum ranging from Gram-positive microorganisms to Gram-negative ones. They exhibit a high antimicrobial activity particularly against Gram-negative bacilli of glucose non-fermentation type, such as Pseudomonas aeruginosa and Acinetobacter. Further, they are highly safe and effective on β-lactamase-producing bacteria (Enterobacters and Citrobacters) which are resistant to cephem of the third generation.

The invention provides an injection composition which comprises the above defined cephalosporin or a non-toxic salt thereof and lactose and/or sodium chloride.

Further the invention provides an injection solution which comprises the above defined composition and an injection carrier.

It is advantageous from the practical point of view that the injection solution comprises lactose and/or sodium chloride in such a total amount as to make a physiological solution. For instance it contains about 0.9 wt.% of sodium chloride, about 5 wt.% of lactose or about 0.45 wt.% of sodium chloride and about 1.5 wt.% of lactose in combination.

The cephalosporin according to the invention is a cephem derivative and is disclosed in U.S. patent application Serial No. 818 824 filed Jan. 14, 1986 and the corresponding EPC patent application No. 86 100 357.2 filed Jan. 13, 1986, now published with EP-A 188 255.

It is, for example, produced by dissolving 2 g of 7β-amino-3-(4-carbamoyl-1-quinuclidinio)methyl-3-cephem-4-carboxylic acid hydrochloride in 40 ml of a mixture of acetonitrile and water mixed at 1:1, adding 2.08 ml of triethylamine to the solution, cooling it with ice, adding thereto 2.55 g of 2-(5-amino-1,2,4-thiadiazol-3-yl)-(Z)-2-methoxyiminoacetylchl stirring the mixture for 50 minutes, adding the reaction mixture to 200 ml of ethanol, separating the deposited solid with filtration, washing the solid with ethanol and isopropylether to obtain 450 mg of the intended product which can be identified with the infrared absorption and the NMR analysis.

Lactose and sodium chloride usable in the present invention are available on the market in, for example, the form of injection. They can be used either singly or in combination. The preferred amounts of them per part by weight of the cephalosporin of the present invention are as follows: When lactose is used singly, the amount thereof is at least 1 part by weight and when sodium chloride is used singly, the amount thereof is at least 0.1 parts by weight. When a combination of them is used, the preferred amounts of them are as follows: in case the amount of lactose is less than 0.25 parts by weight, the amount of sodium chloride is at least 0.1 parts by weight and in case the amount of lactose is at least 0.25 parts by weight, that of sodium chloride is at least 0.05 parts by weight. However, the amounts of them are not particularly limited to these ranges in the present invention. They are incorporated in the injection by dissolving them in water together with the cephalosporin of the present invention.

The powdery injection to be dissolved in situ is provided mainly as a freeze-dried powder. For example, the cephalosporin of the present invention and lactose are dissolved in water, the solution is filtered under sterile conditions, a given amount of the solution is poured in a vial or ampoule and freeze-dried and the vial or ampoule is stopped or sealed by fusion. In another process, the solution is filtered under sterile conditions and freeze-dried into a powder, and a given amount of the powder is packed in a vial of ampoule. At the time of use, water for injection or the like is added to the powder to obtain a solution.

The effect of the present invention is that coloration and reduction in the titer of the cephalosporin of the present invention with the lapse of time can be inhibited when the cephalosporin is used as a powdery injection dissolved in situ. This effect will be provided by an experimental example given below.

The following examples will further illustrate the present invention.

EXAMPLE 1

20 g of the cephalosporin of the present invention and 20 g of lactose were dissolved in distilled water to prepare 100 ml of a solution. The solution was filtered through a membrane filter under sterile conditions. 5-ml portions of the solution were poured into 100-ml vials and freeze-dried. The vials were stopperred.

EXAMPLE 2

20 g of the cephalosporin of the present invention and 4 g of sodium chloride were dissolved in distilled water to prepare 100 ml of a solution. The solution was filtered through a membrane filter under sterile conditions. The resulting solution was poured into a Petri dish to a depth of 10 mm and then freeze-dried under sterile conditions. 900-mg portions of the obtained powder were packed in 20-ml vials and the vials were stopperred.

EXAMPLE 3

20 g of the cephalosporin of the present invention, 1 g of lactose and 4 g of sodium chloride were dissolved in distilled water to prepare 100 ml of a solution. The solution was filtered through a membrane filter under sterile conditions. 10-ml portions of the resulting solution were poured into 10-ml vials and freeze-dried. The vials were stopperred.

EXPERIMENTAL EXAMPLE

Lactose and sodium chloride in amounts corresponding to the weight ratios shown in the column of the weight ratios of additives in Table 1 were added to 20 g of the cephalosporin of the present invention. Water was added thereto to prepare 100 ml of a solution. The solution was filtered through a membrane filter. 5-ml portions of the solution were poured into 10-ml vials and then freeze-dried. The vials were stopperred to obtain samples. The samples were subjected to a storage test at 50° C. for one month and a change in the appearance and the persistence were examined. The persistence was determined from the ratio of the peak heights of the sample and the standard to an internal reference according to high-performance liquid chromatography ($CD_{254}$) wherein the stationary phase comprised YMS-ODS and the mobile phase comprised a mixture of water and methanol (92.8).

Results

The results are shown in Table 1, wherein symbols in the column of "change of appearance" have the following meaning:

++: colored brown,
+: colored yellow or orangy yellow,
±: colored pale yellow, and
—: no color change.

It is apparent from Table 1 that the use of lactose and sodium chloride either singly or in combination is effective in stabilizing the powdery injection of the cephalosporin of the present invention which is to be dissolved in situ. It may be understood that when lactose is used singly, its amount is preferably at least 1 part by weight and when sodium chloride is used singly, its amount is preferably at least 0.1 parts by weight, each per part by weight of the cephalosporin of the present invention. It will be understood also that in case they are used in combination, the amount of sodium chloride is preferably at least 0.1 parts by weight when the lactose is less than 0.25 parts by weight and the amount of sodium chloride is preferably at least 0.05 parts by weight when the lactose is 0.25 parts by weight or more.

TABLE 1

| Weight ratio of additive | | Change of appearance | Persistence (%) |
|---|---|---|---|
| Lactose | Sodium chloride | | |
| 0 | 0 | ++ | 74.7 |
| 0.05 | 0 | ++ | 75.7 |
| 0.25 | 0 | ++ | 77.8 |
| 0.5 | 0 | + | 81.2 |
| 1.0 | 0 | + | 85.0 |
| 0 | 0.05 | ++ | 84.5 |
| 0 | 0.1 | + | 90.6 |
| 0 | 0.2 | + | 93.2 |
| 0.05 | 0.05 | ++ | 85.0 |
| 0.05 | 0.1 | + | 90.0 |
| 0.05 | 0.2 | ± | 92.7 |
| 0.25 | 0.05 | + | 86.6 |
| 0.25 | 0.1 | + | 90.7 |
| 0.25 | 0.2 | ± | 93.2 |
| 0.5 | 0.05 | + | 88.3 |
| 0.5 | 0.1 | — | 90.8 |
| 0.5 | 0.2 | — | 92.5 |
| 1.0 | 0.05 | — | 87.7 |
| 1.0 | 0.1 | — | 89.7 |
| 1.0 | 0.2 | — | 91.9 |

What is claimed is:

1. An injection composition which comprises a cephalosporin having the formula:

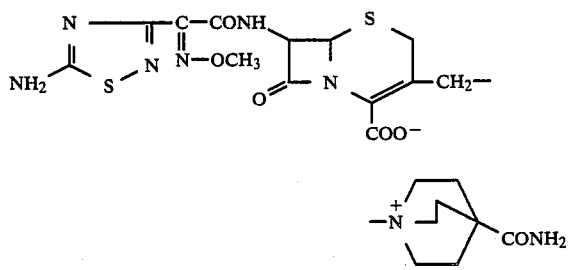
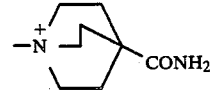

or a non-toxic salt thereof, and one or more members selected from the group consisting of lactose and sodium chloride, with the provisos that (1) if lactose is used singly, the amount there is a pharmaceutically effective amount of at least 1 part by weight, (2) if sodium chloride is used singly, the amount there is a pharmaceutically effective amount of at least 0.1 parts by weight and (3) if both lactose and sodium chloride are used, when the amount of lactose is less than 0.25 parts by weight, the amount of sodium chloride is a pharmaceutically effective amount of at least 0.1 parts by weight and when the amount of lactose is a pharmaceutically effective amount of at least 0.25 parts by weight, the amount of sodium chloride is a pharmaceutically effective amount of at least 0.05 parts by weight, said parts by weight being based on one part by weight of the cephalosporin.

2. An injection composition as claimed in claim 1, which comprises 1 part by weight of the cephalosporin and 1 part by weight of lactose.

3. An injection composition as claimed in claim 1, which comprises 1 part by weight of the cephalosporin and 0.1–0.2 parts by weight of sodium chloride.

4. An injection composition as claimed in claim 1, which comprises 1 part by weight of the cephalosporin, a pharmaceutically effective amount of less than 0.25 parts by weight of lactose and 0.1–0.2 parts by weight of sodium chloride.

5. An injection composition as claimed in claim 1, which comprises 1 part by weight of the cephalosporin, 0.25–1.0 parts by weight of lactose and 0.05–0.2 parts by weight of sodium chloride.

6. The injection composition of claim 1, wherein lactose and sodium chloride are contained in said injection composition in amounts of 0.05 parts by weight and 0.2 parts by weight, respectively, per one part by weight of the cephalosporin contained in said injection composition.

7. The injection composition of claim 1, wherein lactose and, sodium chloride are contained in said injection composition in amounts of 0.25 parts by weight and 0.2 parts by weight, respectively, per one part by weight of the cephalosporin contained in said injection composition.

8. The injection composition of claim 1, wherein lactose and sodium chloride are contained in said injection composition in amounts of 0.5 parts by weight and 0.2 parts by weight, respectively, per one part by weight of cephalosporin contained in said injection composition.

9. An injection solution which comprises an effective amount of the injection composition as defined in claim 8, claim 2, claim 3, claim 4 or claim 5, and an injection carrier.

10. An injection solution as claimed in claim 9, which comprises a member selected from the group consisting of lactose, sodium chloride, and mixtures thereof, in such a total amount as to make a physiological solution.

* * * * *